United States Patent [19]
Weckström et al.

[11] Patent Number: 5,793,043
[45] Date of Patent: Aug. 11, 1998

[54] METHOD AND APPARATUS FOR DETERMINING THE ALCOHOL CONCENTRATION IN A GAS MIXTURE

[75] Inventors: Kurt Peter Weckström, Espoo; Jan Petri Ekström, Helsinki, both of Finland

[73] Assignee: Instrumentarium Oy, Helsinki, Finland

[21] Appl. No.: 774,871

[22] Filed: Dec. 19, 1996

[30] Foreign Application Priority Data

Dec. 29, 1995 [FI] Finland ................................. 956327

[51] Int. Cl.⁶ ............................................. G01N 21/61
[52] U.S. Cl. ................................. 250/339.13; 250/344
[58] Field of Search ............................ 250/343, 339.13

[56] References Cited

U.S. PATENT DOCUMENTS

| | | | |
|---|---|---|---|
| 3,562,524 | 2/1971 | Moore et al. | 250/43.5 |
| 4,268,751 | 5/1981 | Fritzlen et al. | 250/343 |
| 4,914,719 | 4/1990 | Conlon et al. | 250/339 |
| 5,070,245 | 12/1991 | Rantala et al. | 250/343 |
| 5,693,945 | 12/1997 | Akiyama et al. | 250/343 |
| B1 3,792,272 | 7/1986 | Harte et al. | 250/343 |

FOREIGN PATENT DOCUMENTS 2290139  12/1995  United Kingdom .

*Primary Examiner*—Don Wong
*Attorney, Agent, or Firm*—Andrus, Sceales, Starke & Sawall

[57] ABSTRACT

An apparatus for determining the alcohol concentration in a gas mixture, which may contain a number of such interference components that have substantial absorption within the range of the alcohol absorption line to be presently determined, by means of a method based on the absorption of infrared radiation. The apparatus comprises: a radiation source (1); a chamber (4) for receiving a gas mixture (6) to be measured, said chamber being provided with windows (7a, 7b) whereby a radiation (2) passes through the gas mixture; a detector (13) which receives the radiation having passed through the gas mixture and transforms it to an electric state for further processing; between the radiation source and the detector an optical interference filter (10), which has a narrow radiation transmission band and which is pivotable (P) relative to the main traveling direction of radiation for changing the wavelength range of the filter's transmission band. The transmission band of the optical interference filter (10) has a mean wavelength which is within the range of 7.5 μm–12.5 μm and this transmission band of the interference filter (10) has a half-width which is more than 1.5% of said mean wavelength.

16 Claims, 2 Drawing Sheets

METHOD AND APPARATUS FOR DETERMINING THE ALCOHOL CONCENTRATION IN A GAS MIXTURE

BACKGROUND OF THE INVENTION

The present invention relates to a radiation-absorption based method for determining the alcohol concentration in a gas mixture, which may contain a number of such interference components that have substantial absorption within the range of the alcohol absorption line to be presently determined. The method comprises passing a gas mixture through a sample chamber; emitting a ray of light containing a variety of wavelengths from a radiation source through this gas mixture in the sample chamber; allowing the radiation having passed through the gas mixture to travel through an optical interference filter, which has a narrow radiation transmission band and which is inclinable relative to the main radiation traveling direction for changing the wavelength range of the filter transmission band; measuring the intensity of the radiation having passed through said interference filter at more than two different inclinations of the filter; using these transmission values measured at various wavelengths for reducing the effect of interference components on the measuring result and calculating the concentration of alcohol to be determined in the gas mixture. The invention relates also to an apparatus for applying this method.

The invention is particularly directed to a method and apparatus, wherein a method using infrared absorption can be employed for example to measuring the alveolar air of a patient for its alcohol concentration in such a manner that, if necessary, the measuring result can be used for calculating the level of blood alcohol. The apparatus comprises a radiation source, a sample chamber for delivering the alveolar air to be analysed therein, an optical filter for passing the radiation therethrough, and a radiation detector.

The alcohol content of a patient's blood can be measured by a plurality of different methods. The screening type of meters in field use are most of the time based on changes occurring in an electrochemical cell or in a metal oxide semiconductor. These meters are small in size and hand-held, but not necessarily highly accurate. The evidential category measurement is usually performed in a laboratory and the result can be currently obtained of course not only from a blood sample but also from an alveolar air sample on the premise that an air sample contains about 2100 times less alcohol/liter than a blood sample. In practice, the precise factor or coefficient reading is often country-specific, depending on what has been agreed at any given time. In this alveolar-air based procedure, the apparatus generally comprises a gas chromatography device, a fuel cell or an infrared photometer. The latter device has its operation based on the infrared absorption of alcohol. Ethyl alcohol has two major absorption lines, a 3.4 μm band and a 9.4 μm band, which have been used for measuring the alcohol concentration by means of a simple non-dispersive method. The publication U.S. Pat. No. 3,792,272 proposes the use of a preceding adjacent infrared range and the publication U.S. Pat. No. 3,562,524 a subsequent long-wavelength infrared range. Although the publication U.S. Pat. No. 3,792,272 mentions other measurable gases, such as methane and ketone, the purpose is always to measure just one gas at a time. If, for example, the alveolar air contains ketone in addition to alcohol, the device would show a false result since alcohol and ketone have overlapping absorption over the range of 3.4 μm and the device is incapable of distinguishing these gases from each other. The cited publication explicitly points out that no other components of alveolar air except the one to be measured have substantial absorption within the measuring wavelength, which condition is not fulfilled in practice. Similar difficulties are encountered over the 9.4 μm range if the measuring sensor is like the one described in U.S. Pat. No. 3,562,524, which employs a single reference wavelength. This reference is used for compensating for interferences known to occur in a measuring system, such as soiling of the radiation transmitting windows. The described system is not capable of eliminating the effect of gases, such as methyl alcohol, possibly contained in alveolar air and also having absorption over this particular band.

According to the publication U.S. Pat. No. 4,914,719, it would be possible to employ a number of separate narrow-band interference filters for eliminating the effects of interfering gas components. However, the reality has proved that measuring the above-mentioned interference components with separate filters is not only very expensive but also impossible. The immediate vicinity of the ethyl alcohol absorption peak of 9.4 μm cannot be used since the transmission bands of optical filters would be so close to each other that the situation would be non-feasible in terms of manufacturing technique. On the other hand, over the other absorption ranges of said interference components, interferences are caused by other than the above-mentioned interfering gases with the consequence that even more filters would have to be used for in order to account for all interference.

The publication U.S. Pat. No. 5,070,245 discloses a solution using the 3.4 μm range, whose operation is based on shifting the transmission band of a pivotable optical interference filter onto various wavelengths as a result of this pivoting action. In practice, in terms of this type of filter, the absorption peak of a filter has a maximum shift which is about 5% of the mean wavelength of its transmission band. Over the wavelength range employed in the cited publication, this will be less than 200 nm, which nevertheless is a perfectly sufficient magnitude for separating different spectral peaks. A condition is that the transmission band of a filter has a sufficiently narrow width, in practice 0.4–1.5% of the applied wavelength in accordance with the cited publication. True enough, the system described in this cited publication is capable of separating all interference components in such a manner that, for example, the alcohol concentration of alveolar air can be given a value or rating which is sufficiently independent of such components. However, there is a problem that the detector of such an apparatus receives an extremely small intensity share of the radiation emitted by a radiation source, which on the one hand is due to the narrowness of the transmission band of the filter and, on the other hand, to the low degree of maximum transmittance in such filters. Furthermore, such interference filters are difficult to manufacture and hence expensive.

The international standard proposal "Third preliminary draft of an international Recommendation relating to Evidential Breath Analyzers", OIML, Apr. 1992, outlines strict definitions for evidential category analyzers in terms of the interferences or disturbances that can be induced in alcohol measurement by various substances originating from the organism, substitutes exhaust gases, mouthwashes, medicines and other such sources. A common feature for nearly all these substances is that they absorb over the range of 3.4 μm as they are organic compounds containing CH-links. Thus, in practice, all currently used devices, which operate over this wavelength range, do not satisfy the new regulations. As for these more than twenty interfering substances cited in the standard proposal, there are four substances which also absorb significantly over the second alcohol absorption range of 9.4 µm and, thus, the current non-dispersive infrared-absorption based devices possibly operating over this range do not satisfy the new regulations, either.

Therefore, an object of the invention is to provide a radiation-absorption based apparatus and method, capable of producing a sufficiently accurate alcohol concentration rating from a gas mixture which contains a plurality of interference components that have absorption over the wavelength band over which the concentration measurement of a particular alcohol is performed. Thus, the object is to produce such intensity ratings for radiation having passed through a gas mixture which can be used for sufficiently eliminating the effect of interference components on the alcohol measuring result. A second object of the invention is to provide a method and apparatus, capable of producing from alveolar air a reliable concentration measurement of alcohol content irrespective of all interference substances appearing in the above-cited standard proposal. A third object of the invention is to provide a method and apparatus of the above type, capable of supplying radiation from a radiation source to a radiation detector at a sufficiently high efficiency. Hence, the object is to provide a measuring apparatus which is compact, simple and economical, yet reliable in operation.

The above-described problems can be eliminated and the above-defined objects can be achieved by means of a method of the invention which is characterized by what is set forth in the appended claims and by means of an apparatus of the invention which is characterized by what is set forth in the appended claims.

The method and apparatus of the invention take advantage of the angular dependency over the wavelength range of 7.5 µm–12.5 µm of the transmission band of an optical interference filter having a narrow transmission band and for studying the absorption band and its immediate vicinity of alcohol which is the subject of concentration measurement within this range. The transmission band of an employed interference filter has a width which is more than 1.5% of the mean wavelength of an absorption band used for the concentration measurement of alcohol. The measuring information obtained from the immediate peak of the alcohol absorption band and the vicinity thereof is utilized mathematically for compensating for the effects of disturbing substances.

BRIEF DESCRIPTION OF THE SEVERAL VIEWS OF THE DRAWING

The invention will now be described in detail with reference made to the accompanying drawings.

DETAILED DESCRIPTION OF THE INVENTION

Hereinbelow, the invention will be described in reference to the ethyl alcohol absorption line of 9.4 µm, i.e. within the range of 8.7 µm–10.2 µm, but a method and apparatus of the invention can also be applied over other ethyl-alcohol absorption lines within the long-wave infrared range, such as the bands of 8.1 µm and 11.3 µm, the respective wavelength ranges being 7.7 µm–8.4 µm and 10.7µ–12.0 µm. Over the applicable wavelength range of 7.5 µm–12.5 µm a method and apparatus of the invention can also be used for determining the concentration of other alcohols by appropriately selecting the position of the transmission band of an employed interference filter and by appropriately setting those inclinations or attitudes of an interference filter which are used for picking up the transmission readings. It is obvious that the algorithms applied in calculation must be predetermined in the apparatus so as to comply with an employed filter, wavelength range, and an alcohol to be measured. Thus, the following specification must be conceived so as to cover all these options. In this application, the concepts radiation and light are used in an identical meaning, i.e. regardless of whether the radiation is within a visible range or not.

Figure 1:
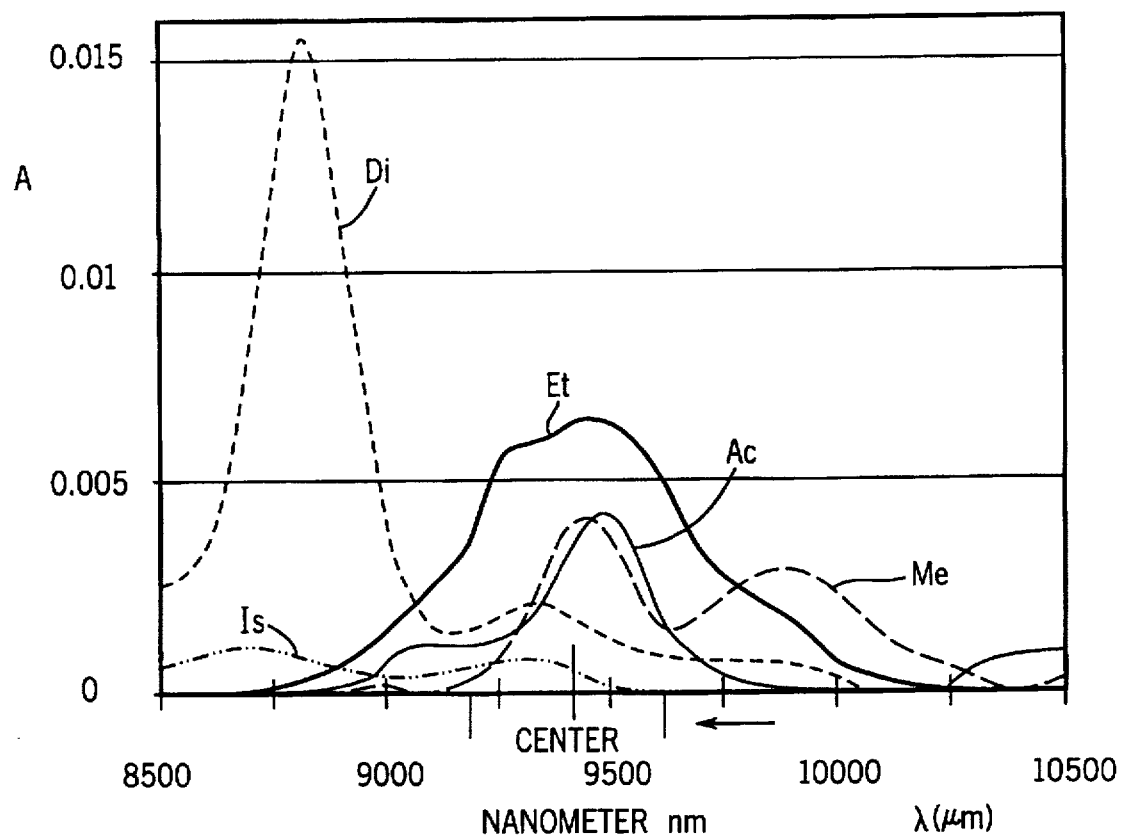
FIG. 1 depicts infrared absorption spectra over the range of 9.4 µm for ethyl alcohol and four substances interfering therewith.

FIG. 1 illustrates the absorbance spectra for ethyl alcohol Et and four strongest interference-causing substances over a spectral range having a wavelength $\lambda$ within the range of 8.5 µm–10.5 µm. Various absorbance values A correspond roughly to the maximum concentrations of certain interference substances set forth in the above-cited standard proposal, the ethyl-alcohol content being 35 µg/100 ml air and the measuring chamber having a length of 100 mm. This alcohol concentration of air equals to about 0.7 promilles as blood alcohol level. The interference components shown in FIG. 1 are methyl alcohol Me, isoprophyl alcohol Is, ethyl acetate Ac, as well as diethyl ether Di. As noted from the spectra, the absorption bands have widths of more than 200 nm, which is typical for this particular spectral range. Within the ethyl-alcohol peak absorption of 9 µm–10 µm, the worst interferences are caused by methyl alcohol Me and ethyl acetate Ac while the share of isoprophyl alcohol Is is relatively insignificant and the greatest influence of diethyl ether Di occurs outside this range. All other disturbing substances have absorbances which are lower and do not extend up to the highest acceptable limit of error set forth in the standard proposal. These substances appear in a gaseous state and include for example carbon dioxide, water, acetone, xylene, pentane, phenol and menthol. It can also be noted from the figure that all components have very low absorbance values. The maximum absorbance value of ethyl alcohol is only about 0.0065, which equals to reading 98.5% as transmission. Thus, in order to produce a good signal and a precise measurement it is important that radiation be in a sufficient amount, that the detector be sufficiently responsive, and that the measuring chamber be of a sufficient length.

A measuring chamber of this invention has been designed by taking advantage of the above observations. Over the wavelength range applied in this invention, the transmission peak of an interference filter and, thus, the entire transmission band has a wavelength shift which is accomplished by an inclination of the filter and which can be about 450 nm, although lesser shifts can also be utilized. At its lowest, the transmission peak shift caused by the inclination of an interference filter must be 210 nm, but preferably it is at least about 300 nm and typically at least about 400 nm. As indicated in FIG. 1, the absorption lines of gas-mixture components have a width of over 200 nm, which means that individual lines are impossible to distinguish even with a narrow filter. A filter provided with a narrow transmission band only transmits a lot less radiation without increasing the distinguishing power. In practice, the smallest conceivable width for the transmission band of an interference filter, explicitly defined as a transmission half-width value, is more than 1.5% of the mean wavelength used in measuring and it would be most preferably more than 1.6% and typically 2%–3% of the applied mean wavelength. As an example, it can be noted that if the object of measuring is e.g. ethyl alcohol and the measuring range has a mean wavelength of 9.4 µm and the transmission band of an interference filter has a half-width which is 2% of this mean wavelength, i.e. 188 nm, the absorption band of the filter has a transition which is about 400 nm from wavelength 9.2 µm to wavelength 9.6 µm. As further noted from FIG. 1, the absorption peak of ethyl alcohol has a width between the half-values of its absorbancies of more than 500 nm. Thus, it is not possible to sweep across the entire absorption line, but it is necessary to settle for a smaller spectral range in the immediate vicinity of the peak. The absorption line peak of an alcohol to be measured may be included and often is included in a wavelength band obtained by the inclination of a filter, but this is not absolutely necessary. For example, the concentration measurement for ethyl alcohol can be implemented by using the transmission-band transition range of 9.5 µm–10 µm for an interference filter. The measuring information will still be sufficient for eliminating the effect of said few interference substances by means of per se known calculating algorithms, which are therefore not further explained in this application.

In view of mathematically eliminating the effect of interference components, the radiation having passed through a sample chamber and an interference filter is measured at several angles of filter inclination, which are at least partially within the angular range of 10°–60°. This cited angle of inclination or deflection is the angle formed by the plane of an interference filter relative to the plane which is orthogonal to the main direction of radiation passing through the sample chamber. Various angles of filter inclination are used for picking up a number of readings which is at least equal to the total number of gas components to be considered in measuring. Thus, if, in addition to alcohol, such as ethyl alcohol, it is necessary to take into account four interference components for reducing the effect thereof to a sufficient degree, i.e. for eliminating the effect thereof, transmission measurement values must be acquired at five different angles of filter inclination, at least some of which are within said inclination range of 10°–60°. If it is known that a gas mixture may not contain more than e.g. two interference components, it will be sufficient to obtain measurement values at three different angles of filter inclination, at least some of which are within said inclination range of 10°–60°. Thus, the number of employed angles of inclination is at least equal to the total number of an alcohol to be measured and reference components N to be noted, in other words N+1. However, it would be perfectly acceptable to acquire measurement values for calculation at even higher number of filter inclinations, such as N+2, N+3 etc.

A method of the invention as described is in principle adaptable to measuring the concentration of any alcohol at all in any gas mixture at all. In its most preferred application, however, the method is used for determining the alcohol concentration from alveolar air, and then especially from exhalation air whose alcohol content depends on the level of blood alcohol, as pointed out above. Therefore, the above-described measurement values of the invention are picked up at that point of exhalation when the exhalation air comes from deep in the lungs and, thus, the question is about so-called alveolar exhalation air.

Figure 2:
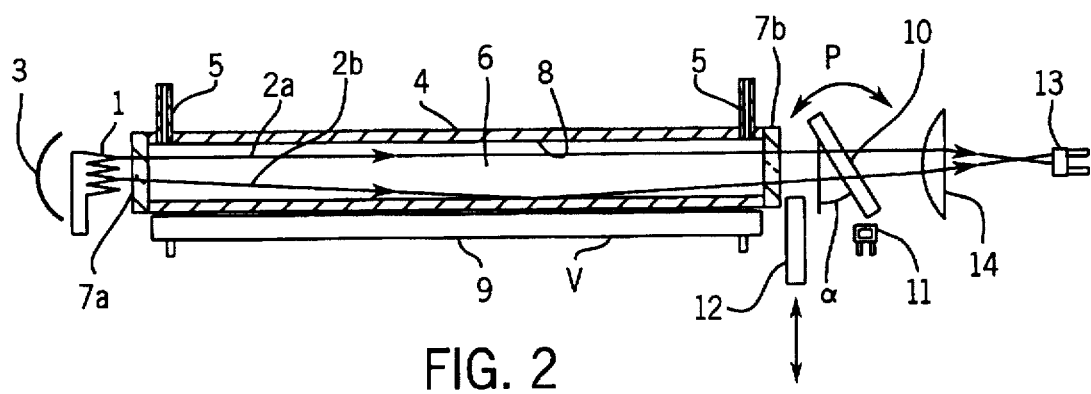
FIG. 2 shows schematically in a radiation-oriented section a first embodiment of the invention for an apparatus suitable for the accurate measurement of alcohol.

FIG. 2 illustrates one apparatus design suitable for the accurate measurement of alcohol. The maximization of a radiation 2 emitted by an infrared source 1 is pursued by means of appropriate optical components, such as e.g. a mirror 3, since the radiation efficiency of several radiation sources is relatively poor over the applied 9.4 µm range. The radiation 2 is delivered into a sample chamber 4 which is provided with gas outlets 5 for picking up a sample 6 of alveolar gas. The sample chamber 4 is elongated, preferably has a length of more than 100 µmm, for achieving a sufficient alcohol absorbance level. Both ends of the chamber are provided with windows 7a and 7b transmissive to expended radiation. The exploitable radiation 2 is substantially parallel to the sample chamber or, preferably, does not diverge therefrom by more than 10°. Thus, the radiation 2 has a main direction which is substantially parallel to a ray 2a of the sample chamber extending lengthwise thereof. Hence, the radiation source 1 and the optics 3 associated therewith should most preferably be designed in such a manner that as much as possible of the radiation emitted by the source would be exploitable. Such rays having passed through the sample chamber may travel linearly without touching an inner wall 8 of the sample chamber 4, such as the ray 2a, or, depending on the length of the chamber, such rays may reflect once or twice from the inner chamber wall 8, such as a ray 2b, but the combined mean direction of even those rays is parallel to the length of the sample chamber. Thus, the inner wall 8 of the sample chamber 4 can be made of a reflective material, such as metal, but, since the rays have a very large angle of reflection, the reflection coefficient need not necessarily be very high in order to produce a sufficient reflection. In terms of corrosion and heatability, stainless steel is a preferred material but some other material, such as a suitable plastics material, would be nearly as useful and, as a result of favourable manufacturing costs, could be a good choice, especially if the service life required of a sample chamber is short. In a normal case, the sample chamber is directly supplied with a sample from the alveolar air of a patient without pre-filtering and reduction of moisture. For this reason, the sample chamber 4 must have a sufficiently high temperature in order to preclude condensation. The sample chamber 4 can be heated e.g. as shown in FIG. 1 by thermally connecting therewith a heating element 9, typically a heating resistance. In view of minimizing the consumption of heating power, it is preferred that the sample chamber or the entire sensor be thermally insulated from the environment.

An optical filter 10 provided with a narrow transmission band comprises most preferably an interference filter with a high angular dependance and having a bandwidth of more than 1.5% and preferably more than 2% of the mean wavelength of the filter's transmission band in order to achieve a sufficient signal level. The interference filter is inclined in a direction P for producing an operating angle α, which is an angle between the plane of the filter 10 and a plane V which is orthogonal to the main direction of the radiation 2. In practice, the operating angle α of a filter is most of the time within the range of 10°–60°, and the radiation having passed through the filter is measured at a number (N+1) of different angles a which is at least equal to the total number of an alcohol and interference components having a substantial effect on the measurement thereof. The number of measurement readings can be higher than N+1 for improved accuracy as long as the measuring time remains within reasonable limits. According to the invention, regardless of the number of measurement readings produced, at least one of those must be picked up while the filter lies within the above-mentioned angular range of 10°–60°. Measurement values can also be picked up while the filter operating angle α lies outside said angular range, but usually the number of such measurement values is no more than one or two. The angle α of the filter 10 is monitored by means of a detector 11. A preferred way of deflecting the filter 10 in the direction P, which in the figures is parallel to the image plane, is for example to employ a stepping motor, which is not shown in the figures and which pivots back and forth within the required angular range.

Since, at least from time to time, the adjustment of darkness level in a measuring system requires a total shut-off of radiation, it is possible to fix a shutter 12 in the path of radiation. Such a shutter can be a separate element but may also be connected to the above-mentioned stepping motor, which would block the progress of radiation if the value of angle α is about 90°. It would also be possible to rotate the filter 10 continuously with a motor, although this would mean spending unnecessary extra time for by-passing non-operative angles.

Figure 3:
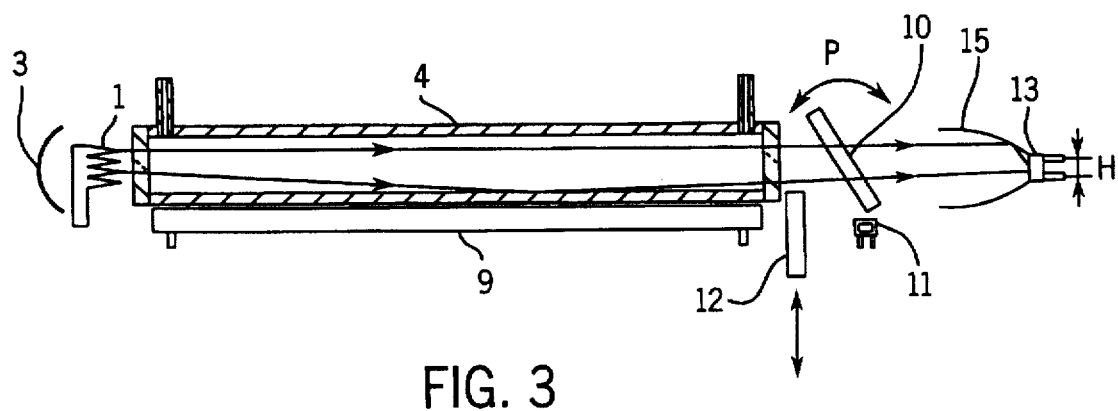
FIG. 3 shows schematically in a radiation-oriented section a second embodiment of the invention for an apparatus suitable for the accurate measurement of alcohol in a view similar to FIG. 1.

The radiation having passed through the sample chamber 4 and the filter 10 is detected by means of a detector 13. Since the proper operation of the interference filter 10 requires nearly parallel light, the use is made for example of an optical system 14 for focusing a certain angular distribution on the surface of the detector 13. The apparatus would function even without this optical system as the sample chamber 4 must be relatively long and the filter 10 has a transmission band which is relatively wide with respect to the wavelength shift caused by the angular difference between rays arriving through the sample chamber. However, in order to produce as good a signal as possible from the detector, the optics 14 are indeed necessary. The optical system may preferably comprise a lens 14, which is transmissive to radiation to be measured and which is fitted between the interference filter 10 and the detector 13, but it could just as well be an appropriately shaped concave mirror 15, as shown in FIG. 3. The focal distance of the optical system 14 and the size of the radiation sensing detector 13 determine the angular distribution which the radiation to be detected will end up within. If, for example, the focal distance is 10 mm and a vertical detector side H is 0.7 mm, the angles of radiation will be within ±2° when the filter is deflected or rotated in a plane parallel to the image plane P. This guarantees a highly sufficient wavelength resolution with the filter 10 operated even at quite large angles α. In the horizontal direction, i.e. in a direction orthogonal to the pivoting plane P of the filter 10 (in a direction orthogonal to the image plane), the detector 13 may be wider, as the angular distribution of radiation changes very little in that direction upon rotating the filter. In an exemplary case, it could be even 3 mm without major effects on the resolution. This serves to improve the signal level. The rays, which subsequently make up the intensity arriving in the detector 13, must have angles of incidence on the interference filter 10 not to diverge from each other more than by about ±10° for providing a sufficient resolution, preferably the angles of incidence of a beam of rays diverge by no more than ±4° and typically by the above-mentioned ±2°. This means, thus, that the rays of an individual beam of rays diverge from each other no more than by the above-mentioned differences in the angles of incidence. Thus, the question is about an angle which is totally different from what is referred to in this application as an angle of filter inclination, which also achieves the variation of an average angle of incidence (according to general practice, the angle of incidence is an angle between the normal of surface and the incident ray) within the range of at least 10°–60° in accordance with one aspect of the invention. Quite generally, the angle of filter inclination and thus the average angle of incidence may fluctuate within the range of 0°–90°. It should be appreciated that, in reality, the interference filter may have beams of radiation falling thereupon at angles of incidence even more different from each other than the above-mentioned range, but those are not allowed to proceed to the detector 13. It is obvious that a large-surface detector can be limited to an equal size by means of a shutter gap, not shown in the figures, but such a solution is not as preferred in terms of signal noise.

In order that the measuring signals received from the detector 13 be usable, it is necessary in every situation to know a signal produced by darkness or total absorption as well as a signal without absorption induced by a sample. A darkness-produced signal is obtained by using the above-mentioned shutter 12 and it is the same for all angles α formed by the filter 10, provided that the system is designed to preclude the interference of possible diffused light. If the detection of a signal is effected e.g. by using a thermal detector, such as a thermocouple, the relevant dark signal is in practice substantially zero. A radiation-produced signal without absorption of a sample gas cannot be assessed without a separate measurement of a zero gas. Such a zero gas or reference gas is for example an air sample picked up from the environment, which does not absorb radiation over the measuring band. In practice, the suction of a zero gas into the sample chamber 4 and measuring the same prior to anlyzing a sample gas does not cause problems and, indeed, the measurement of alcohol according to the above-cited standard must be carried out exactly that way regardless of the analyzing method.

The signals received from the detector 13 are linearized and analyzed by means of some multi-gas analysis method well known in the literature as such. A sufficient result is generally a reliable alcohol concentration reading, although there could be an alarm for possible interference gases. An alarm could also be useful for example in such a case that some previously unknown disturbance is present within the wavelength range used for analysis. In concentration calculation, such a disturbance would primarily appear as poor compatibility with the calculating algorithm. As depicted in FIG. 1, methyl alcohol Me and ethyl acetate Ac have nearly an identical absorption peak at about 9.4 μm and, thus, in calculation it might be impossible to distinguish these from each other. However, this is of no significance since the effect on the reading of ethyl alcohol Et remains negligible. Thus, the only properly identified and correctly measured gas will be alcohol. Of course, it is also perfectly possible, if necessary, to identify or endeavour to identify the substances of interference components.

The above describes but a few examples of how the immediate vicinity of the absorption peak of alcohol can be used for accurate concentration analysis by rotating or deflecting a narrow-band optical interference filter. Of course, the apparatus can be designed to be even a considerably different type. For example, mirrors can be used for passing a ray of light several times through a sample chamber containing a gas mixture to be measured in view of increasing the absorbing distance without adding to the external dimensions of the apparatus. It is also possible to have a ray of light travel into and out of a sample chamber through a single window, either at one or more locations on the window. Other structural options are also conceivable.

We claim:

1. A radiation-absorption based method for determining the concentration of a given alcohol compound in a gas mixture, which gas mixture may contain one or more interference components, the interference components exhibiting substantial absorption of radiation, the wavelengths of which are in a wavelength range which includes the wavelength of radiation that can be used to determine the concentration of the given alcohol compound, said method comprising the steps of:

providing a sample of the gas mixture;

passing radiation through the gas mixture, the wavelength properties of the radiation being such as to include wavelengths in a range of between 7.5 µm to 12.5 µm and including, within the range, radiation of a wavelength that can be used to determine the concentration of the given alcohol compound;

applying the radiation exiting the gas mixture to an optical interference filter, the filter having a radiation transmission band defining a mean wavelength of the radiation used to determine the given alcohol compound concentration, the transmission band of the filter having a width which is more than 1.5% of the mean radiation wavelength;

inclining the optical interference filter to a plurality of positions for shifting the transmission band of the filter, each of the positions being angularly displaced by a different amount with respect to the direction along which the radiation exits the gas mixture, the number of inclined positions being at least equal to the numerical sum of the given alcohol compound plus the number of interference components with substantially different absorption spectra with respect to each other;

detecting the intensity of the radiation transmitted through the filter at the plurality of inclined filter positions; and determining the concentration of the given alcohol compound in the gas mixture from the detections made at the plurality of angularly displaced positions, the transmission band shifts resulting from different filter inclinations enabling the effects of interfering components in the gas mixture to be reduced in the determination of the concentration of the given alcohol compound.

2. The method as set forth in claim 1 characterized in that the radiation applying step is further defined as applying the radiation to an optical interference filter having a transmission bandwidth which is at least 2% of the mean wavelength of the radiation used to determine the alcohol compound concentration.

3. A method as set forth in claim 1 characterized in that the inclining step is carried out over angles of filter inclination, as measured with respect to a plane that is orthogonal to the exit direction of the radiation, that are at least within a range of 10°–60°.

4. A method as set forth in claim 1 characterized in that the radiation passing step is further defined as passing radiation including wavelengths in a selected one of the following wavelength ranges: 7.7 µm to 8.4 µm; 8.7 µm to 10.2 µm; and 10.7 µm to 12.0 µm.

5. A method as set forth in claim 4 wherein the radiation passing and applying steps are further defined as passing radiation having wavelengths in a range between 8.7 µm to 10.2 µm, wherein the optical filter to which the radiation is applied defines a mean wavelength of concentration determining radiation of 9.4 µm, and wherein said method is further defined as a method for measuring the concentration of ethyl alcohol.

6. A method as set forth in claim 1 wherein the step of inclining the optical filter is further defined as inclining the optical filter to shift the transmission band of the filter by at least about 200 nm.

7. A method as set forth in claim 6 wherein the step of inclining the optical filter is further defined as inclining the optical filter to shift the transmission band of the filter by at least about 400 nm.

8. A method as set forth in claim 1 wherein the determining step is further defined as using the detections made at the plurality of angularly displaced positions to eliminate the effects of the interfering components in the determination of the concentration of the given alcohol compound.

9. A method as set forth in claim 1 further defined as a method for determining the concentration of a given alcohol compound in a gas mixture comprising the exhalation air of a subject and wherein the detecting step is further defined as carried out at that stage of exhalation when the provided gas mixture is alveolar air.

10. An apparatus for determining, on the basis of radiation absorption properties, the concentration of a given alcohol compound in a gas mixture, which gas mixture may contain one or more interference components, the interference components exhibiting substantial absorption of radiation, the wavelengths of which are in a wavelength range which includes the wavelength of the interference components radiation that can be used to determine the concentration of the given alcohol compound, said apparatus comprising:

a sample chamber containing the gas mixture;

a radiation source providing radiation, the wavelength properties of the radiation being such as to include wavelengths in a range of between 7.5 µm to 12.5 µm and including, within the range, radiation of a wavelength that can be used to determine the concentration of the given alcohol compound, the radiation being passed through the gas mixture in said sample chamber;

an optical interference filter receiving the radiation exiting the sample chamber, said optical filter having radiation transmission band defining a mean wavelength of the radiation used to determine the given alcohol compound concentration, the transmission band of the filter having a width which is more than 1.5% of the mean radiation wavelength;

means for inclining the optical interference filter to a plurality of positions for shifting the transmission band of the filter, each of the positions being angularly displaced by a different amount with respect to the direction along which the radiation exits the sample chamber, the number of inclined positions being at least equal to the numerical sum of the given alcohol compound plus the number of interference components with substantially different absorption spectra with respect to each other; and means for detecting the intensity of the radiation transmitted through the filter at the plurality of inclined filter positions and for determining the concentration of the given alcohol compound in the gas mixture from the detections made at the plurality of angularly displaced positions, the transmission band shifts resulting from different filter inclinations enabling the effects of interfering components in the concentration to be reduced in the determination of the concentration of the given alcohol compound.

11. The apparatus as set forth in claim 10 characterized in that the optical interference filter has a transmission bandwidth which is at least 2% of the mean wavelength of the radiation used to measure the alcohol compound concentration.

12. An apparatus as set forth in claim 10 characterized in that the said means for inclining said filter inclines said filter over angles of filter inclination, as measured with respect to a plane that is orthogonal to the exit direction of the radiation, that are at least within a range of 10°–60°.

13. An apparatus as set forth in claim 10 characterized in that the radiation source is further defined as providing radiation including wavelengths in a selected one of the following wave length ranges: 7.7 µm to 8.4 µm; 8.7 µm to 10.2 µm; and 10.7 µm to 12.0 µm.

14. An apparatus as set forth in claim 13 wherein said radiation source provides radiation having wavelengths in a range between 8.7 µm to 10.2 µm, wherein said optical filter defines a mean wavelength of measuring radiation of 9.4 µm, and wherein said apparatus is further defined as one for measuring the concentration of ethyl alcohol.

15. An apparatus as set forth in claim 10, characterized in that said optical interference filter is fitted between said sample chamber and said detection means and that the apparatus further comprises an optical assembly between said interference filter and said detection means, for collecting, in the detection means radiation rays, whose angles of incidence on the interference filter differ from each other by no more than about ±10°.

16. An apparatus as set forth in claim 15 wherein the angular displacement of the filter occurs in a plane parallel to the exit direction of the radiation and wherein said detecting means has a width orthogonal to said plane which is greater than the height (H) of said detecting means parallel to said to collect said radiation means.

* * * * *